United States Patent [19]

Kurtz et al.

[11] 4,261,362

[45] Apr. 14, 1981

[54] UNDERWATER DRAINAGE APPARATUS WITH REDUCED DEAD AIR SPACE

[75] Inventors: Leonard D. Kurtz, Woodmere; Robert E. Bidwell, Long Island, both of N.Y.

[73] Assignee: BioResearch Inc., Farmingdale, N.Y.

[21] Appl. No.: 73,224

[22] Filed: Sep. 7, 1979

[51] Int. Cl.³ .............................................. A61M 1/00
[52] U.S. Cl. ................................................... 128/276
[58] Field of Search ........................ 15/353; 137/205; 128/276, 277, 278, 762, 767

[56] References Cited

U.S. PATENT DOCUMENTS

| | | |
|---|---|---|
| 3,363,626 | 1/1968 | Bidwell et al. ...................... 128/276 |
| 3,363,627 | 1/1968 | Bidwell et al. ...................... 128/276 |
| 3,559,647 | 2/1971 | Bidwell et al. ...................... 128/276 |
| 4,015,603 | 4/1977 | Kurtz et al. ......................... 128/276 |

Primary Examiner—Robert W. Michell
Assistant Examiner—J. L. Kruter
Attorney, Agent, or Firm—Larson, Taylor and Hinds

[57] ABSTRACT

An underwater drainage apparatus is provided with an underwater seal formed by fluid from the pleural cavity of the patient. The dead air space within the underwater drainage apparatus is reduced to a minimum by dividing the collection chamber into a plurality of compartments and providing seals between the compartments which are dissolved when liquid from the preceding compartment reaches the dissolvable seal. A passageway is provided in the air space directly above the underwater seal chamber to connect to the outlet to suction and a one way valve is provided in this passageway.

15 Claims, 5 Drawing Figures

UNDERWATER DRAINAGE APPARATUS WITH REDUCED DEAD AIR SPACE

BACKGROUND OF THE INVENTION

This invention relates to a surgical drainage system and more particularly, to an apparatus designed to drain fluids from a body cavity.

It is essential for normal breathing that the space within the pleural cavity surrounding the lungs be free of liquid and be subject to a negative pressure so as to draw the lungs outwardly to fill the pleural cavity. Any invasion of the pleural cavity such as lung surgery, foreign objects piercing the ribcage or pleurisy, generate fluids in the pleural cavity which obstruct normal breathing and it is necessary to provide means for removing these fluids and at the same time to maintain the desired degree of negative pressure within the pleural cavity.

The basic apparatus which has been used for this purpose is an apparatus such as shown in U.S. Pat. Nos. 3,363,626 and 3,363,627. This apparatus is known as an underwater drainage apparatus and provides basically three chambers, one chamber comprising a collection chamber for collecting the fluids drained from the pleural cavity, a second chamber known as an underwater seal chamber which protects the pleural cavity from being subject to atmospheric pressure, and a third chamber known as a pressure manometer chamber which regulates the degree of negative pressure within the pleural cavity. This type of apparatus has been highly successful in both removing fluids from the pleural cavity and in maintaining the desired degree of negativity within the pleural cavity. However, the attachment of an underwater drainage apparatus to a patient's pleural cavity in effect enlarged the pleural cavity to the extent of the size of the collection chamber. This so called "dead air space" within the collection chamber caused the patient additional effort in breathing. While under ordinary circumstances this additonal effort would not be a problem but, in the case of a patient in a weakened condition or a child, the additional air space imposed by the collection chamber may cause severe difficulties in breathing.

The drainage system disclosed in U.S. Pat. No. 4,015,603 was developed to provide a solution to the problems outlined above. Specifically, the underwater drainage apparatus disclosed in Patent No. 4,015,603 limits the dead air space created by attachment of a drainage apparatus by locating the underwater seal directly at the end of the thoracotomy tube. Thus, the volume of the collection chamber itself did not constitute an additional volume in the pleural cavity. This device has proven highly successful but, the location of the underwater seal chamber at the lower end of the thoracotomy tube created a further problem in certain unusual circumstances. In the case of a patient having a blockage in the bronchial tubes, such that the patient was having severe problems in getting air into the lungs, exceedingly high negativity was being created in the pleural cavity. Such high negativity caused the fluid in the underwater seal to be drawn upwardly through the thoracotomy tube and, if the degree of negativity was sufficiently high, it was possible for fluid to reenter the pleural cavity. This condition of fluid from the underwater seal chamber reentering the pleural cavity could cause infection or otherwise create problems for the patient. In addition, it was possible to entirely lose the seal provided by the underwater seal chamber during periods of high negativity in the pleural cavity. The loss of the water seal has the potential for serious damage in the event the suction becomes disconnected or the device is used as a two bottle system with the collection chamber open to atmosphere.

SUMMARY OF THE INVENTION

The present invention provides a surgical drainage system which overcomes the difficulties noted above with respect to previous underwater drainage apparatus. The present invention provides an apparatus wherein the underwater seal chamber is located at the end of the thoracotomy tube with the seal chamber being shaped with a sloping bottom wall and provided with a sump so that all of the liquid within the underwater seal will drain to the lower end of the thoracotomy tube and thus, so long as there is any liquid within the underwater seal chamber, a seal will be maintained. In addition, the collection chamber is provided with a series of dissolvable barriers so that the air space above the underwater seal is limited to a very small proportion of the total volume of the collection chamber. Furthermore, the connection to suction is made directly above the underwater seal with a oneway valve provided in the passageway between the underwater seal chamber and the connection to suction so that in the event high negativity develops within the patient's pleural cavity, the negativity required to draw up fluid up through the thoracotomy tube from the underwater seal chamber is substantially increased and it is not possible for the patient to develop sufficient negativity to either break the underwater seal or draw fluid up into the pleural cavity.

Thus, the present invention provides for the reduction of dead air space achieved in Patent 4,015,603 but, avoids the possible problems associated with the use of that apparatus including drawing liquid from the underwater seal chamber into the pleural cavity and loss of the underwater seal during periods of high negativity in the patient's pleural cavity.

Additional features and advantages of the present invention will be apparent from a consideration of the following detailed description of the preferred embodiments of the invention in connection with the accompanying drawings.

DETAILED DESCRIPTION OF THE PREFERRED EMBODIMENT

Figures 1, 2, 3:
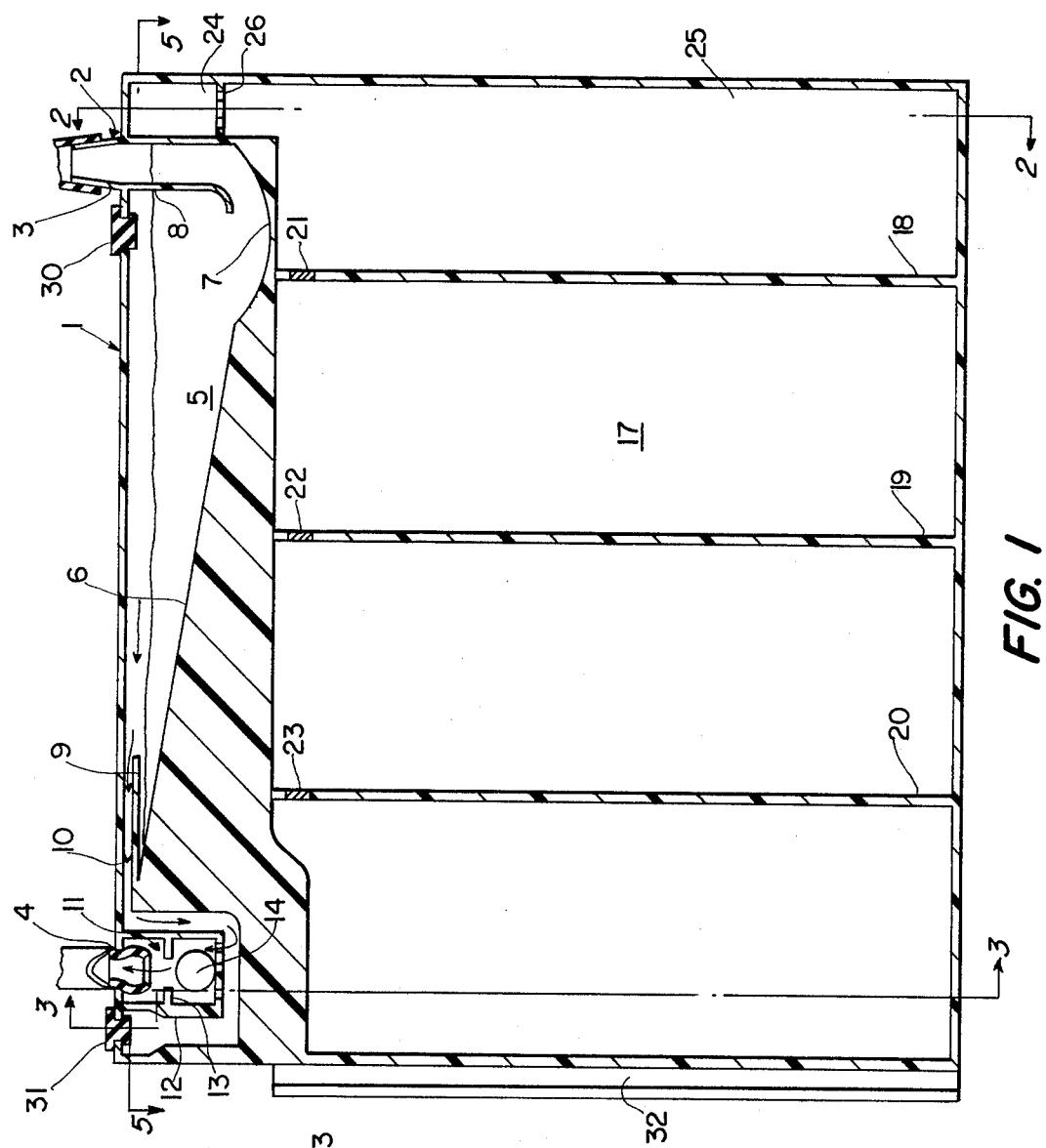
FIG. 1 is an elevational partial sectional view of an underwater drainage apparatus according to the present invention.
FIG. 2 is a sectional view along the lines 2—2 of FIG. 1.
FIG. 3 is a sectional view along the lines 3—3 of FIG. 1.
Figure 4:
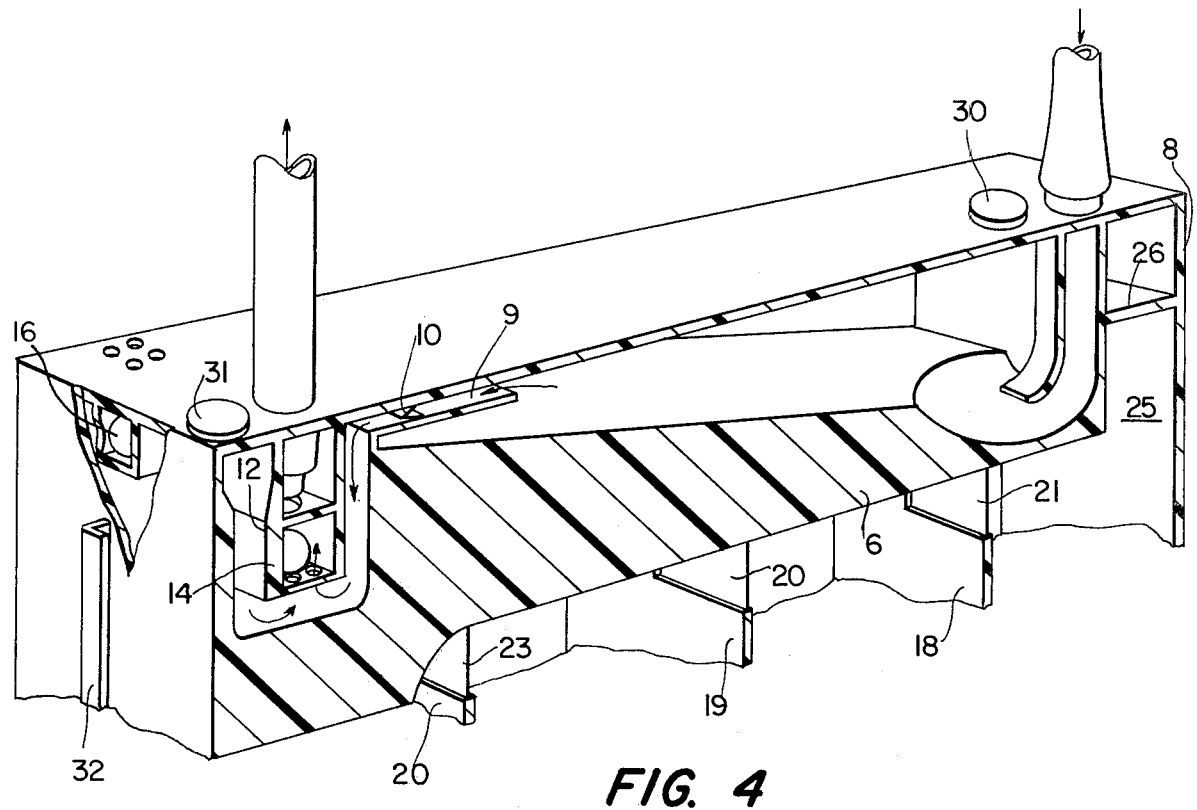
FIG. 4 is a partial perspective view of the top portion of the underwater drainage apparatus.
Figure 5:
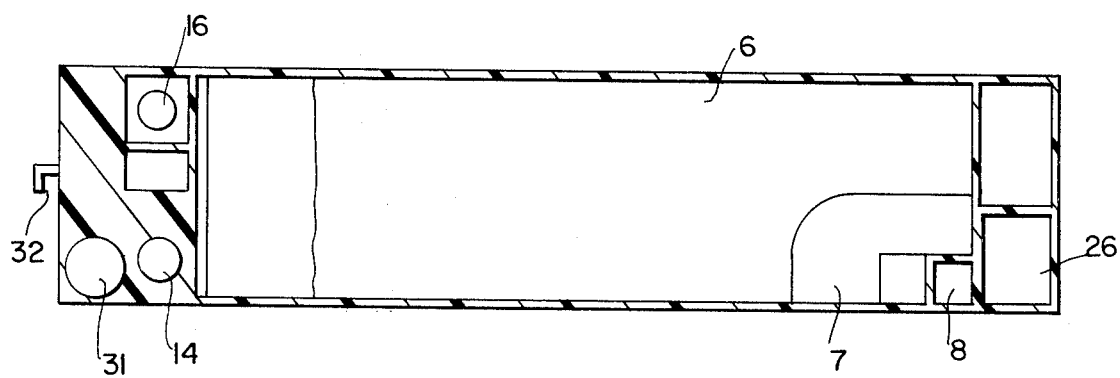
FIG. 5 is a sectional view along the lines 5—5 of FIG. 1.

Referring now more specifically to the drawings, there is shown in FIG. 1 an underwater drainage apparatus comprising a container 1 which may be formed of a rigid transparent plastic material or the like. This container is provided with a patient inlet tube 2 which has a nozzle portion 3 thereon which is adapted to be connected with a thoracotomy tube and connected with a patient's pleural cavity. The container 1 is further provided with an outlet 4 which is adapted to be connected with a tube leading to a suction pump. Alternatively, the outlet 4 may be left open to atmosphere in the event the device is used as a two bottle system.

Formed in the upper end of the container 1 is an underwater seal chamber 5. The underwater seal chamber is provided with a sloping bottom wall 6 which drains to a sump area 7 disposed beneath the inlet 2. It can be seen that the nozzle portion 3 of the inlet 2 is provided with a downwardly extending tubular portion 8 which terminates in the sump 7 of the underwater seal.

Adjacent the outlet 4 in the underwater drainage apparatus, there is provided a passageway 9 which extends into the underwater seal chamber 5. It will be noted that the bottom wall of this passageway extends a substantial distance into the underwater seal chamber to prevent liquid from the underwater seal from splashing into the passageway 9. Within the passageway 9 there is provided a oneway valve 10 which is similar to a "Heimlich" valve comprising a pair of elastic membranes having a slit therebetween which will permit flow of gases from the underwater seal chamber towards the outlet 4 but, which will prevent the reverse flow of gases. Beneath the outlet 4 there is formed a chamber 11 and disposed within this chamber 11 beneath the outlet 4 is a valve cage 12. The valve cage 12 is provided with a valve seat 13 and a ball valve 14 is disposed beneath the seat 13. In the event liquid from the underwater seal should inadvertently enter the chamber 11, the ball valve 14 will float on this liquid and move upwardly within the valve cage until the ball valve seats on the valve seat 13 to prevent the flow of liquid through the outlet 4 into the vacuum pump. Referring to FIG. 3, it can be seen that there is provided within the chamber 11 a valve seat 15 with a ball valve 16 normally seated thereon. The upper end of chamber 11 above the valve seat 15 is open so that when the ball valve 16 is unseated, there is provided a passageway direct to atmosphere. The ball valve 16 provides a positive pressure relief valve to atmosphere in the event the pressure within the pleural cavity should exceed atmospheric pressure.

The collection chamber 17 is divided by a plurality of partitions 18, 19 and 20 into a series of compartments. The partitions 18, 19 and 20 extend across the width of the underwater drainage apparatus and extend from the bottom wall to the upper end of the collection chamber. There is provided an opening in each partition adjacent the top of the collection chamber and within this opening there is disposed a polyvinyl alcohol film as shown at 21 in partition 18, 22 in partition 19 and 23 in partition 20.

A passageway 24 is formed between one end of the underwater seal chamber and compartment 25 of the collection chamber. Within this passageway, there is disposed a polyvinyl alcohol film 26 which normally maintains the passageway 24 closed.

In operation, the thoracotomy tube is attached to the nozzle portion 3 of the inlet to the underwater drainage apparatus and the outlet 4 is connected with a regulated vacuum suction which is adapted to maintain a regulated suction within the underwater drainage apparatus. Alternatively, the outlet 4 may be left open to atmosphere. Liquid from the patient's pleural cavity will flow through the thoracotomy tube into the underwater seal chamber 5. When this chamber is filled, the liquid will overflow into the passageway 24 so as to dissolve the polyvinyl alcohol film 26. Thus, liquid from the pleural cavity will flow into the compartment 25. When the compartment 25 is filled, the liquid level will reach the polyvinyl alcohol film 21 which will dissolve and permit fluid to overflow the partition 18 and pass into the succeeding compartment. In this manner, the dead air space within the collection chamber is maintained at an absolute minimum, the maximum air being the air space above the water seal and one compartment of the collection chamber. Thus, should a blockage occur within a patient's pleural cavity so that a high degree of negativity occurs within the pleural cavity causing liquid to flow upwardly through the thoracotomy tube, the vacuum within the air space in the collection chamber will increase substantially thus preventing the liquid from reaching the pleural cavity.

The oneway valve 10 prevents air from being drawn from the chamber 11 or the outlet back into the underwater seal chamber in the event of high negativity within the patient's pleural cavity. Thus, the valve 10 contributes to minimizing the liklihood that liquid could be drawn up through the thoracotomy tube to reach the pleural cavity. There is provided a rubber diaphragm 30 through which a needle can be inserted to take liquid samples from the underwater seal chamber if desired.

In addition, there is provided a rubber diaphragm 31 together with a guide 32 on the side of the underwater drainage apparatus for the addition of a pressure manometer chamber. The means for adding the pressure manometer chamber is the subject matter of a copending application filed concurrently herewith.

Obviously, many modifications and variations of the present invention are possible in light of the above teachings.

What is claimed as new and is desired to be secured by Letters Patent is:

1. An underwater drainage apparatus comprising a container including, a collection chamber and an underwater seal chamber, said underwater seal chamber being disposed at the upper end of the container, a tube extending outwardly of the container from the lower portion of the underwater seal chamber, the outer end of the tube being adapted to be connected with the pleural cavity of a patient, an overflow passageway extending from the underwater seal chamber to the collection chamber, said underwater seal chamber having a bottom wall shaped to slope towards the end of the tube and means for restricting the height liquid within the underwater seal may pass upwardly through the tube so as to prevent liquid from reentering the pleural cavity of the patient, said means comprising reducing the dead air space within the collection chamber and above the underwater seal so that the maximum negativity developed within the pleural cavity cannot draw liquid within the underwater seal upwardly greater than one foot.

2. An underwater drainage apparatus according to claim 1 wherein said last named means comprises a dissolvable element disposed between the underwater seal and the collection chamber.

3. An underwater drainage apparatus according to claim 1 and further including partition means dividing said collection chamber into a series of individual compartments and dissolvable elements disposed in said partition means to close succeeding compartments in said series of compartments until the preceding compartments are filled.

4. An underwater drainage apparatus according to claim 1 and further including means for connecting the container with a source of suction, said means including an outlet from the container, and a passageway connecting said outlet with the underwater seal chamber.

5. An underwater drainage apparatus according to claim 4 and further including a oneway valve in said passageway, said one way valve permitting flow from the underwater seal chamber to the outlet and preventing flow in the opposite direction.

6. An underwater drainage apparatus according to claim 4 and further including ball valve means in said outlet to prevent flow of liquid through the outlet.

7. An underwater drainage apparatus comprising, a container including a collection chamber and an underwater seal chamber, said underwater seal chamber being disposed at the upper end of the container, a thoracotomy tube extending outwardly of the container from the lower portion of the underwater seal chamber, an overflow passageway extending from the underwater seal chamber to the collection chamber, dissolvable means disposed in said passageway for closing said passageway until liquid overflows from the underwater seal chamber, and an outlet passageway from the container whereby when the thoracotomy tube is connected with a patient's cavity, liquid from the cavity will initially fill the underwater seal chamber and further liquid from the cavity will cause the underwater seal chamber to overflow into the overflow passageway and dissolve said dissolvable means to open the passageway to the collection chamber.

8. An underwater drainage apparatus according to claim 7 and further including partition means dividing said collection chamber into a series of individual compartments and additional dissolvable means in said partition means to close succeeding compartments in said series of compartments until the preceding compartments are filled.

9. An underwater drainage apparatus according to claim 7 and further including means for connecting the container with a source of suction, said means including an outlet from the container, and a passageway connecting said outlet with the underwater seal chamber.

10. An underwater drainage apparatus according to claim 9 and further including a one way valve in said passageway, said one way valve permitting flow from the underwater seal chamber to the outlet and preventing flow in the opposite direction.

11. An underwater drainage apparatus according to claim 7 and further including ball valve means in said outlet to prevent flow of liquid through the outlet.

12. An underwater drainage apparatus comprising, in combination, an integral container having an opening in the upper end and a tube formed in the opening for connection with a thoracotomy tube to interconnect the apparatus with the pleural cavity of a patient, an underwater seal chamber formed within the upper end of said container, said underwater seal chamber having a sloping bottom wall to form shallow and deep end portions, said deep end portion being disposed below said tube, said tube extending into said underwater seal chamber to the bottom thereof, a passageway in the underwater seal chamber adjacent the shallow end portion, an outlet from said container in communication with said passageway, a collection chamber within said container disposed beneath said underwater seal chamber, and an overflow passageway from the underwater seal chamber into the collection chamber.

13. An underwater drainage apparatus according to claim 12 and further including a one way valve in the passageway between the underwater seal chamber and the outlet, said one way valve permitting fluid flow from the underwater seal chamber to the outlet and preventing fluid flow in the reverse direction.

14. An underwater drainage apparatus according to claim 12 and further including dissolvable means disposed in the overflow passageway between the underwater seal chamber and the collection chamber, said dissolvable means initially closing the overlow passageway and dissolving in contact with liquid to open the passageway.

15. An underwater drainage apparatus according to claim 14 and further including partition means dividing said collection chamber into a series of separate compartments and dissolvable closure elements disposed in said partitions so that said compartments are sequentially opened as preceding compartments in the series are filled with liquid.

* * * * *